United States Patent [19]

Roos et al.

[11] Patent Number: 5,675,227

[45] Date of Patent: Oct. 7, 1997

[54] DEVICE FOR MANEUVERING A RADIOLOGY APPLIANCE

[75] Inventors: Hartog Roos, Brookfield, Wis.; José Garrote, Madrid, Spain

[73] Assignee: GE Medical Systems, Buc, France

[21] Appl. No.: 626,752

[22] Filed: Apr. 2, 1996

Related U.S. Application Data

[63] Continuation of Ser. No. 126,175, Sep. 23, 1993, abandoned.

[30] Foreign Application Priority Data

Sep. 25, 1992 [FR] France .................. 92 11475

[51] Int. Cl.⁶ ................. H02D 5/28; F16D 3/06
[52] U.S. Cl. .................. 318/446; 318/563; 192/130; 192/129 A; 307/326; 378/117
[58] Field of Search ................. 318/560, 563, 318/564, 565, 600, 603, 446, 445; 378/114, 115, 116, 117; 307/326, 327, 328; 192/129 R, 130, 129 A; 246/186

[56] References Cited

U.S. PATENT DOCUMENTS

| | | | |
|---|---|---|---|
| 4,032,789 | 6/1977 | Workman | 378/117 |
| 4,135,247 | 1/1979 | Gordon et al. | 364/414 |
| 4,170,735 | 10/1979 | Codina et al. | 378/117 |
| 4,251,730 | 2/1981 | Cushman et al. | 378/40 |
| 4,260,894 | 4/1981 | Neumann | 250/445 |
| 4,386,320 | 5/1983 | Lafrance | 378/117 |
| 4,442,486 | 4/1984 | Mayer | 364/200 |
| 4,689,492 | 8/1987 | Peteuil | 307/142 |
| 4,775,993 | 10/1988 | Kaul et al. | 378/114 |
| 4,991,193 | 2/1991 | Cecil et al. | 378/117 |
| 5,206,894 | 4/1993 | Makrinos et al. | 378/114 |

FOREIGN PATENT DOCUMENTS 0 244 562  11/1987  European Pat. Off.
2163308  2/1986  United Kingdom.

*Primary Examiner*—John W. Cabeca
*Attorney, Agent, or Firm*—Nilles & Nilles, S.C.

[57] ABSTRACT

A safety system including two command buttons (7, 8) spaced apart from one another geographically, and obliging an operator to use both his hands to control a radiology appliance, or one hand and a foot, is completed by a protocol including, on a single button (7), a short pulse followed by a long pulse during which the maneuver is carried out. It is shown that, under these conditions, the stress on the operator is lower and he is less fatigued

23 Claims, 1 Drawing Sheet

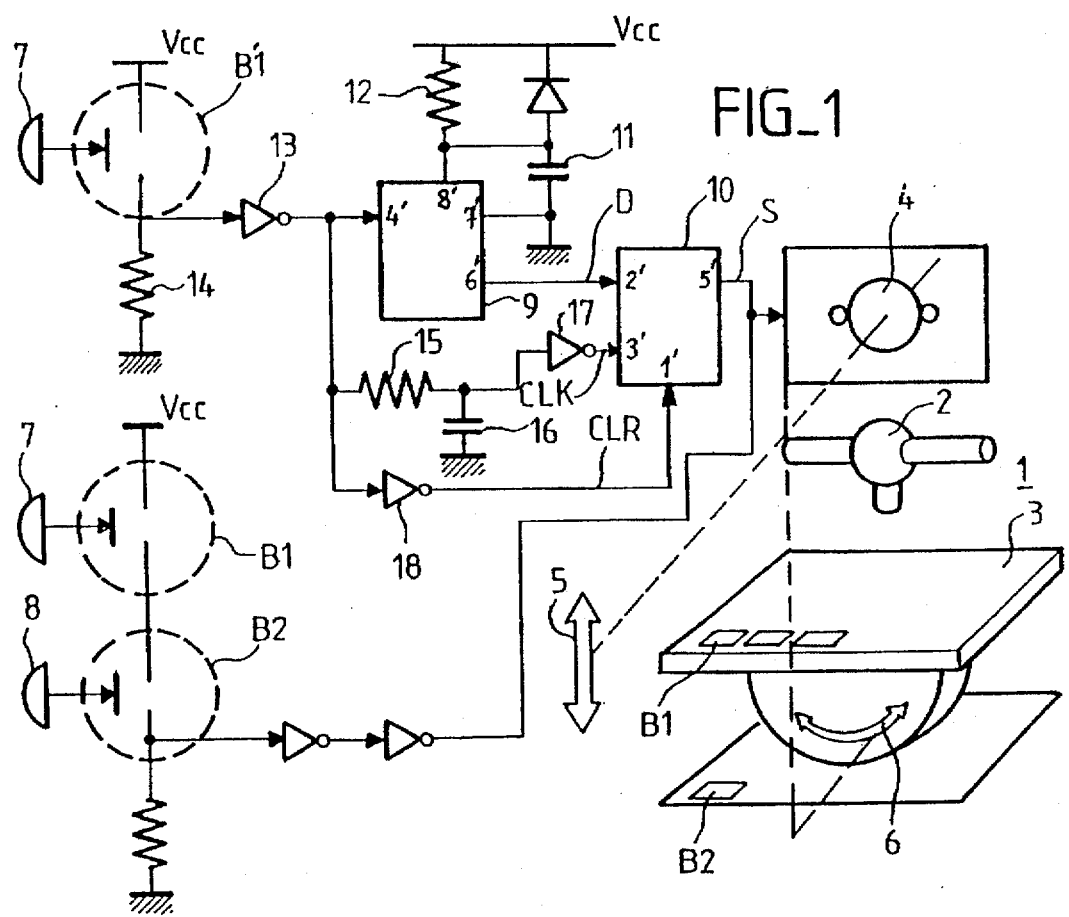
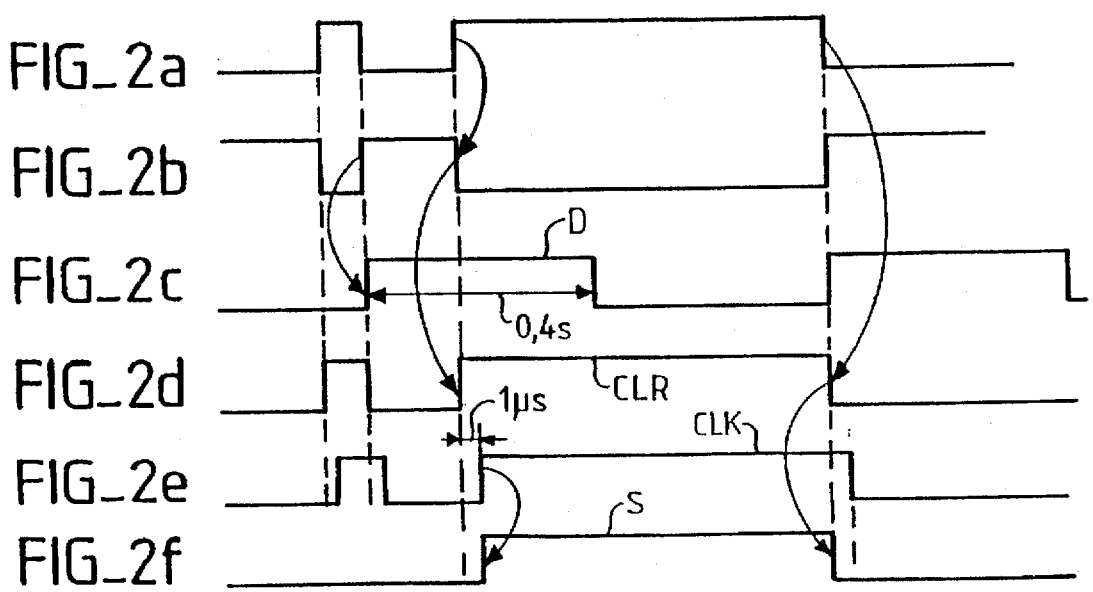

DEVICE FOR MANEUVERING A RADIOLOGY APPLIANCE

This application is a continuation of application Ser. No. 08/126,175, filed Sep. 23, 1993, now abandoned.

BACKGROUND AND SUMMARY OF THE INVENTION

1. Field of the Invention

The subject of the present invention is a device for maneuvering a radiology appliance and, more particularly, for triggering and handling this maneuvering. The invention aims to render the operations of maneuvering various radiology appliances more ergonomic, without thereby compromising safety when maneuvering these appliances.

2. Discussion of the Related Art

Among radiology appliances are distinguished essentially, on the one hand, radiology tables on which patients are placed, and, on the other hand, X-ray tubes and their accessories. A radiology table has to be displaced, raised or lowered or even tilted in order to make the patient assume the best positions with respect to the X-ray tube. An X-ray tube and/or its accessories have to undergo movements of the same order. Normally, in order to maneuver the table, the tube or the accessories, an operator acts on one or more control buttons visible on the front or upper face of the table. It is possible for the operator or the patient inadvertently to actuate these control buttons. This may be prejudicial to the quality of the negative obtained and may even be dangerous for the patient, the operator or the appliance. In order to avoid such drawbacks, it is provided that the starting of a motor for maneuvering each of these appliances dictates simultaneous action on the control button chosen as well as on another control button, for example, placed on the floor and on which the operator can press with his foot. The absence of action on either one of these buttons prevents the maneuver. In these conditions, it can easily be understood that the patient and even the operator cannot inadvertently bring about an awkward movement.

This type of solution exhibits a drawback, however, related to the place where each of the two control buttons is located. On the one hand, such a safety system necessitates the use of both hands at once, or one hand and a foot, giving rise to excessive fatigue for the operator. On the other hand, while monitoring two simultaneous actions, the attention paid by the operator to the displacement of the table, or of the appliance, is limited, since he must continuously give his attention to keeping control in two places and monitoring the movement.

OBJECTS AND SUMMARY OF THE INVENTION

The object of the invention is to remedy this drawback by proposing the exercise of essentially one action, carried out over time, for example by separate pulses of a particular type. In practice, the simplest sequence which has been devised consists in asking the operator to apply a short pulse on a control unit and, after release, to apply a long pulse for as long as he wants the command to be held. The sequence or the protocol chosen may, needless to say, be different. There may especially be two short pulses followed by a long holding pulse during which the maneuvering motor will be running.

In one improvement, arrangements are made to mount the safety protocol according to the invention in parallel with a control button common to the safety system of the state of the art. In this way it still remains possible to control the table in a conventional manner or, when the operator so desires, in the manner according to the invention. It is then apparent that, by not calling for any double action by the operator, but only his hand or only his foot, the attention of the operator may more easily be directed to the monitoring of the maneuver and the stopping of the radiology appliance when the radiology appliance reaches the position which it was desired to make it adopt.

Hence the subject of the invention is a device for triggering and handling the maneuvering of a radiology appliance including a control unit, which can be actuated by an operator, linked to a motor for maneuvering the appliance, which includes a detector for detecting the application to this unit of at least two commands, consecutive in time, the first command being short and being followed by a prolonged command, and a circuit for starting the motor depending on a signal delivered by the detector.

BRIEF DESCRIPTION OF THE DRAWINGS

The invention will be better understood upon reading the description which follows and upon examining the figures which accompany it. The latter are given only by way of indication and in no way limit the invention. The figures show:

FIG. 1: a maneuvering device in accordance with the invention;

FIGS. 2a to 2f: timing diagrams of electrical signals which can be used in a preferred variant of the invention.

DETAILED DESCRIPTION OF THE PREFERRED EMBODIMENT

FIG. 1 shows a device for triggering and handling the maneuvering of a radiology appliance according to the invention. It includes a radiology appliance (1) equipped here, in the example, with an X-ray tube (2) and with a radiology table (3) capable especially of undergoing, by the action of one or more motors (4), vertical (5), tilting (6) or other displacements. In the state of the art, the motor (4) is started by simultaneously actuating two switches B1 or B2 which transmit a reference potential ($V_{cc}$) to the motor (4) by way of a command. The switches B1 and B2 are controllable by an operator who presses on buttons (7) or (8).

In the invention, another switch B'1 has been placed on a control button, for example the button (7); the switch B'1 is thus actuated preferably at the same time. The switch B'1 is linked to a detector in order to detect the application to the button (7) of at least two commands which are consecutive in time. The first command is a short command and is followed by a prolonged command.

The detector is capable of recognizing that the first command is short and that the second is prolonged. In this case the detector transmits an output signal S, which drives the motor (4), to a circuit (not represented) for starting the motor. The starting circuit is not represented because it is conventional. It includes relays.

In one preferred example, the detector includes a monostable latch (9) linked to a set (10) of logic gates, the output of which delivers the signal S. In the example, the monostable latch (9) is an integrated circuit of the 74HC4538 type from the SGS THOMSON MICROELEC- TRONICS company. In one example, this monostable latch delivers a pulse, the duration of which is 0.4 seconds. For this purpose, the latch 9 is connected by its terminals (7') and (8') to a capacitor (11), the capacitance of which is 2.2 microfarads and is supplied by a power supply source $V_{cc}$ (preferably at 5 volts) (on its terminal 8') via a resistor (12), the value of which is 220 kohms. In order to avoid spurious pulse transmissions, the resistor (12) is mounted in parallel with a 1N4007-type diode. In these conditions the monostable latch (9) delivers a signal D visible in FIG. 2c, the duration of which is 0.4 seconds after the appearance of a positive state change. In a way, the monostable latch (9) memorizes, for a short duration, the fact that the first pulse has been produced.

In the example represented, the signal available at the output of the switch B'1 is equal to 0 volts while the operator is not pressing on the button (7). When he presses on the button (7), the signal delivered by the switch B'1 is equal to $V_{cc}$. FIG. 2a shows, in these conditions, the shape of the output signal from the switch B'1 during a first short pulse and then during a second long pulse. The long pulse serves for the actual command to the motor (4). As long as it is maintained, the motor (4) brings about the expected displacement of the radiology appliance. Owing to this particular configuration, an inverter (13), which delivers a signal, visible in FIG. 2b, complementary to the signal delivered by the switch B'1, has been interposed between the switch B'1 and the monostable (9). It would have been possible to dispense with the inverter (13) with a different configuration of the switch. For example, here, the switch is connected, on the one hand, to the power supply source $V_{cc}$ and, on the other hand, to a resistor (14). The resistor (14) is connected to ground. It would have been possible to connect the switch to ground, on the one hand, and to the resistor (14) on the other hand. The other terminal of the resistor (14) would have been connected to the power supply $V_{cc}$. In this case a signal of reversed polarity would have been available, usable as such by the monostable latch (9).

The signal delivered by the monostable latch (9) is introduced onto an input (terminal 2') of a set of logic gates (10). In one example, this set of logic gates consists of an integrated circuit of 74HC74 type from the same manufacturer as before. This set of logic gates receives, on the one hand, (on its terminal 2') the signal D, and, on the other hand, on its zero-reset inputs (1') a signal CLR visible in FIG. 2d and identical in every way to the signal introduced via the switch B'1, as well as a clock signal CLK connected to the terminal (3') of the integrated circuit (10). The signal CLK visible in FIG. 2e is slightly delayed with respect to the signal CLR. This delay is brought about by the presence of an RC circuit including a resistor (15) which, in one example, is equal to 1 kohm, and a capacitor (16), the capacitance of which is equal, in one example, to 1 nanofarad. The effect of this circuit is to delay the transmission of the clock signal with respect to the zero-reset signal by about one microsecond. Having regard to the presence of the inverter (13) in each of the branches for transmission of the clock signal CLK and of the zero-reset signal CLR, inverters such as (17) and (18) have been added. The delay of one microsecond in the clock signal CLK prevents the signal D from actually being transmitted during the first pulse during which the button (7) is actuated. The delay of one microsecond serves to avoid the bounce effects of the integrated circuits.

The operation of the circuit presented is as follows. At the end of the first command or command pulse, on the rising edge of the signal delivered by the inverter (13), the monostable latch (9) latches up and produces a signal D, positive at $V_{cc}$, for about 0.4 seconds FIG. 2c. Upon the application of the second long command or command pulse, the signal CLR returns to 1, enabling the operation of the set of logic gates (10). As soon as the delayed clock signal passes in its turn to the gates (10), the circuit (10) delivers a pulse of the signal S: FIG. 2f. This pulse lasts as long as the signal CLR lasts, thus as long as the action on the button (7) lasts. As soon as this action ceases, the signal S falls back to zero and the motor (4) is no longer driven.

It will be noted moreover that, if the second pulse is applied by the operator on the button (7) after the enabling duration imposed by the monostable latch (9), the signal D will have fallen back to zero and consequently will not allow motor (4) to start. To some extent, a certain dexterity and a certain rapidity are necessary during actions on the button (7). This constitutes the expected safety aspect. Any operation which is not sufficiently rapid would not have the effect of starting the motor (4).

In practice, the configuration of FIG. 1 shows that it is easily possible to use both systems, the system of the state of the art and that of the invention, at the same time. If a single push is applied to the buttons (7) and (8), the system will operate conventionally. In effect, the two switches B1 and B2 controlled by these buttons are connected to the output of the circuit (10). If two successive pushes are applied according to the invention on the button (7), the system will operate according to the invented mechanism. There exist, in the trade, multiple switches which are controlled by a single action on a single button. Moreover, if it is desired to change the three-pulse protocol including two short and one long, it is sufficient to make up the signal D from a logic AND part connected to two multivibrators, one of which receives a delayed signal delivered, for example, by the first.

There are, needless to say, as many detectors as there are buttons which can be used to actuate the various movements of the radiology appliance. It will be noted, moreover, that, if the operator makes a mistake and presses three times instead of pressing only twice, and if the third command is long, the maneuver will take place during the third command and possibly also a little during the second. This is not troublesome.

We claim:

1. A device for triggering and handling the maneuvering of a radiology appliance including a manually actuated switch linked to a motor for maneuvering the appliance, which includes a detector 1) for detecting the application to said manually actuated switch of first and second command pulses, consecutive in time, the first command pulse being short and the second command pulse being prolonged and 2) for generating a signal only when both of said command pulses are applied to said unit and only when said second command pulse is applied within a designated period following termination of said first command pulse, said second command pulse having a duration which is longer than said designated period and being maintained as long as appliance handling is needed, and a circuit, coupled to said detector, for starting the motor only when said signal is delivered by the detector.

2. The device as claimed in claim 1, which includes, in the detector, a set of logic gates in a relationship with the control unit and with a monostable circuit.

3. The device as claimed in claim 1 which includes, in the detector, a retarder circuit for preventing the starting of the motor for a designated period after initiation of said second, prolonged command.

4. The device as claimed in claim 1, wherein said switch establishes a connection between a reference potential and said detector and establishes a series connection of said reference potential to another switch, for controlling said maneuvering motor in another way.

5. The device as claimed in claim 1, wherein said designated period is less than one second.

6. The device as claimed in claim 5, wherein said designated period is about 0.4 seconds.

7. The device as defined in claim 1, wherein said switch comprises a control button.

8. A device for triggering the operation of a motor which maneuvers at least a portion of a radiology appliance, said device comprising:

(A) a manually actuated switch;

(B) a detector which is electronically coupled to said switch and which generates an output signal only in the event of the consecutive application of at least first and second command pulses to said switch, wherein said first command pulse has a first duration, said detector generates said output signal only if said second command pulse is initiated within a designated period following termination of said first command pulse, and wherein said second command pulse 1) has a second duration which is longer than said designated period and 2) is maintained as long as appliance maneuvering is needed, and wherein said second duration is relatively long when compared to said first duration; and (C) a circuit which is electronically coupled to said detector and which applies motive power to said motor only when said output signal is generated by said detector.

9. The device as defined in claim 8, wherein said detector comprises (A) a monostable latch electronically coupled to said switch; and (B) a set of logic gates electronically coupled to said switch and to said monostable latch.

10. The device as defined in claim 9, wherein said detector further comprises a retarder circuit which prevents the generation of said output signal and thus the application of motive power to said motor for a designated period of time after initiation of said second command pulse.

11. The device as defined in claim 10, wherein said retarder circuit comprises an RC circuit disposed between said switch and said set of logic gates.

12. The device as defined in claim 9, further comprising (A) an inverter located between and electronically connected to said switch and said monostable latch and (B) a resister electronically connected to said switch.

13. The device as defined in claim 8, further comprising a power source electronically connected to said monostable latch, and wherein said detector further comprises a resister, an inverter, and a capacitor disposed between said power source and said monostable latch.

14. The device as defined in claim 8, wherein said switch comprises a control button.

15. The device as defined in claim 8, wherein said switch comprises a first switch, and further comprising (A) a second switch, (B) a source of a reference potential, and (C) a second circuit coupled to said second switch, and wherein application of said first switch establishes (1) a connection between said reference potential and said detector and (2) a series connection of said reference potential to said second switch, thereby permitting the application of motive power to said motor immediately upon simultaneous operation of said first and second switches.

16. The device as defined in claim 8, wherein said designated period is less than one second.

17. The device as defined in claim 16, wherein said designated period is about 0.4 seconds.

18. A method of triggering the operation of a motor which maneuvers at least a portion of a radiology appliance, said method comprising:

(A) applying at least first and second consecutive command pulses to a manually actuated switch;

(B) detecting the application of said first and second consecutive command pulses to said switch and generating an output signal only after initiation of said second command pulse and only if said second command pulse is initiated within a designated period following termination of said first command pulse, wherein said designated period is less than one second and wherein said second command pulse 1) has a duration which is longer than said designated period and 2) is maintained as long as appliance maneuvering is needed; and (C) applying motive power to said motor from a first circuit only when said output signal is generated.

19. The method as defined in claim 18, wherein said designated period is about 0.4 seconds.

20. The method as defined in claim 18, further comprising retarding the generation of said second output signal for a designated period of time after initiation of said second command pulse, thereby avoiding bounce effects.

21. The method as defined in claim 20, wherein said second designated period of time is about one microsecond.

22. The method as defined in claim 18, further comprising applying motive power to said motor from a second circuit, even in the absence of the generation of said output signal, upon the simultaneous application of command pulses to said switch and to a second manually actuated switch.

23. The method as defined in claim 18, wherein said first command pulse has a second duration and said duration of said second command pulse is relatively long when compared to said second duration.

* * * * *